United States Patent
Westlake, III et al.

[11] Patent Number: 5,317,932
[45] Date of Patent: Jun. 7, 1994

[54] SAMPLE PROBE

[75] Inventors: Theodore N. Westlake, III; Duane K. Wolcott, both of Baton Rouge, La.

[73] Assignee: The Dow Chemical Company, Midland, Mich.

[21] Appl. No.: 843,687

[22] Filed: Feb. 28, 1992

[51] Int. Cl.[5] .............................................. G01N 1/10
[52] U.S. Cl. ............................ 73/864.73; 73/863.23; 73/863.86
[58] Field of Search ............ 73/864.73, 864.74, 866.5, 73/863.86, 863.81, 863.23, 863.41, 31.07, 61.55, 61.54, 64.56

[56] References Cited

U.S. PATENT DOCUMENTS

| | | | |
|---|---|---|---|
| 4,375,170 | 3/1983 | Sperry, III et al. | 73/866.5 X |
| 4,516,425 | 5/1985 | Chollet et al. | 73/861.65 X |
| 4,569,228 | 2/1986 | Bellgardt et al. | 73/866.5 |
| 4,594,903 | 6/1986 | Johnson | 73/863.86 X |
| 4,631,961 | 12/1986 | Yohe et al. | 73/866.5 |
| 4,640,128 | 2/1987 | Lewis | 73/866.5 |
| 4,715,217 | 12/1987 | Coyne et al. | 73/61.1 C |
| 4,818,870 | 4/1989 | Griffiths | 73/864.73 X |
| 4,819,478 | 4/1989 | Melcher | 73/61.1 C |
| 4,832,034 | 5/1989 | Pizziconi et al. | 128/632 |
| 4,837,161 | 6/1989 | Stevens et al. | 436/52 |
| 4,944,180 | 7/1990 | Tou et al. | 73/38 |
| 4,957,620 | 9/1990 | Cussler | 210/635 |
| 5,001,938 | 3/1991 | Downie | 73/866.5 X |
| 5,085,087 | 2/1992 | Franck et al. | 73/864.73 |
| 5,090,257 | 2/1992 | Bruce | 73/863.23 X |
| 5,161,417 | 11/1992 | Strong et al. | 73/863.86 |

OTHER PUBLICATIONS

Brodbelt et al., "In Vivo Mass Spectrometric Determination of Organic Compounds in Blood with a Membrane Probe," *Anal. Chem.*, Feb. 1, 1987, vol. 59, No. 3, pp. 454–458.

Cox, "Membrane Inlets for On-Line Liquid Phase Mass Spectrometric Measurements in Bioreactors," *Mass Spectrometry in Biotechnological Process Analysis and Control*, Plenum, Press, 1987, pp. 63–65.

*Primary Examiner*—Tom Noland

[57] ABSTRACT

An apparatus for use in determining the presence and/or concentration of one or more selected materials in a matrix stream of materials within a process pipe, reactor or other process vessel, including (a) a support member having a first, internal end for inserting into the matrix stream when the apparatus is placed in service and a second end positioned externally of the pipe, reactor or other vessel in use, wherein the support member defines a groove therein of which at least a portion extends into the matrix stream in use, and (b) a conduit, for example a capillary membrane, positioned and supported substantially wholly within at least that portion of the groove in the support member which extends into the matrix stream in use.

25 Claims, 8 Drawing Sheets

SAMPLE PROBE

BACKGROUND OF THE INVENTION

The present invention relates to devices for detecting, monitoring and/or measuring low-level concentrations of certain materials within a complex matrix stream or aggregation of flowable materials. In one of several, more particular aspects, the present invention relates to such devices which employ permeation membrane or diffusion membrane tubing in some fashion to collect and isolate these certain materials from within the stream or aggregation.

Tubular membranes have been suggested for use in this capacity in a number of analytical devices, and are particularly of interest for use in separating out those components of a complex stream which might adversely affect a gas or liquid chromatograph or other analytical device if one attempted to analyze the complex stream directly. Exemplary of these devices are those described in U.S. Pat. Nos. 4,715,217 to Coyne et al. and 4,944,180 to Tou et al., both of which are commonly-assigned and owned with the present invention.

The Coyne et al. patent relates a membrane-assisted analytical chemistry method for determining the concentration of an organic compound in an aqueous matrix, in which a tubular membrane is encased in a protective perforated stainless steel tube and placed in a magnetically stirred sample container. A receiving fluid passes through the selectively permeable membrane tubing and collects the organic compound permeating through the membrane, and transports the organic compound to an analytical means for determining the concentration of the organic compound in the stirred sample.

U.S. Pat. No. 4,944,180 to Tou et al. describes a system for measuring the permeation rate or organic molecules across a polymer film, in which a flow-through semipermeable tubular membrane probe provides an interface to a mass spectrometer. The probe consists of a semipermeable tubular membrane which extends coaxially through an elongated cylindrical bore of the tee. The side arm of the tee is connected directly to the mass spectrometer. Organic molecules permeating through the film being tested are carried through the membrane, and these organic molecules on permeating from within the membrane are communicated to the mass spectrometer.

From a process control and monitoring perspective, each of these analytical devices is sub-optimal in that samples must be drawn from a given process stream and then analyzed. The collection of the materials of interest through a membrane is necessarily time-consuming of itself, but the process of drawing samples creates additional delay in assessing changes in the process stream and altering the composition or course of the process stream responsive to these changes.

Still other shortcomings of these devices in a process control context include the possible safety and exposure hazards associated with the increased handling and repeated sample-drawing required in the use of these devices, along with the additional expense in materials and time for sampling and handling samples from a process stream. Additionally, in many instances, it may be difficult or impossible to draw an appropriate sample even if the drawing could be safely done. The compound of interest could be unstable, and could be lost between the process vessel and the device. Or, the process may be under vacuum or at high or varying pressures.

Tubular membranes have been utilized in on-line systems for the direct, real-time monitoring of certain low-level materials in a matrix stream of materials, but in limited circumstances. For example, in U.S. Pat. No. 4,832,034 to Pizziconi et al., a length of capillary membrane is inserted directly into the blood stream of a patient for monitoring biological reactions and trends. A similar device is described in Brodbelt et al., "In Vivo Mass Spectrometric Determination of Organic Compounds in Blood with a Membrane Probe", Anal. Chem., 1987, Vol. 59, pages 454–457, wherein a membrane probe is supported internally over a portion of its length by the insertion of a nylon monofilament and is used in vivo.

Other membrane-covered probes have been used apparently for monitoring and controlling the reactions in bioreactors. In Cox, "Membrane Inlets for On-Line Liquid Phase Mass Spectrometric Measurements in Bioreactors", *Mass Spectrometry in Biotechnological Process Analysis and Control,* Plenum Press, 1987 at pages 63–65 is described a perforated stainless steel tube which is capped at one end and which is inserted into the core of silicone rubber tubing. Other devices are described which appear to be of a fundamentally similar nature.

The tubular membrane devices briefly described in the preceding two paragraphs possess a common shortcoming, however, in that the membranes in each are exposed to abrasion or cutting by particulates or other suspended debris (e.g., flakes of rust from the inside of a process pipe) in a matrix stream, or to damage or destruction in pinch points within a pipe, reactor or other process vessel. Further, the influence of the flowing sample stream along and around the membranes of these devices may cause an elongation and distortion of the membranes, and this elongation and distortion of the membranes in turn can be expected to alter the response of the membrane-detector system.

In sum, there is a significant need for an effective tubular membrane-based device for the on-line detecting, monitoring and/or measuring of low-level concentrations of certain materials within a complex industrial process stream, in which the membrane is protected from damage by the debris often found in such environments and is not distorted by a high flow rate in the stream.

SUMMARY OF THE PRESENT INVENTION

The present invention provides an apparatus for use in determining the presence and/or concentration of one or more selected materials in a significantly larger matrix stream or aggregation of flowable materials within a process pipe, reactor or other process vessel. The apparatus of the present invention in this aspect comprises (a) a support member having a first, internal end for inserting into the matrix stream or aggregation when the apparatus is placed in service and a second end positioned externally of the pipe, reactor or other process vessel in use, wherein the support member defines a groove therein of which at least a portion extends into the matrix stream or aggregation in use, and (b) a conduit positioned and supported substantially wholly (and preferably wholly) within at least that portion of the groove in the support member which extends into the matrix stream or aggregation in use.

"Conduit", as used in describing an element of the present invention above and elsewhere herein, is intended to embrace permeation membrane and diffusion membrane tubing as well as, for example, optical fibers and the like.

With respect to such optical fibers, it has been appreciated in conjunction with the present invention that such fibers could (like the aforementioned tubular membranes) be inserted into a matrix stream or aggregation of flowable materials for determining the presence and/or concentration of one or more selected materials therein by known attenuated total reflectance (ATR) methods. By such methods the one or more selected materials of interest adhere or are captured on the exposed surface of the clad or unclad fiber, and are analyzed through the selective absorption by these materials of near-infrared light traveling over the length of the optical fiber.

With the tubular membranes and optical fibers alike, the apparatus of the present invention permits contact with the stream or aggregation of flowable materials and to the materials therein while effectively protecting a given "conduit" from the types and causes of damage described previously.

DETAILED DESCRIPTION OF THE PREFERRED EMBODIMENTS

Referring now to FIGS. 1-7 and 10, two alternative embodiments of the basic apparatus are depicted. A first embodiment or elements thereof is shown in FIGS. 1-4, while a preferred alternative embodiment and elements thereof are addressed in FIGS. 5-7 and 10.

Figure 1:
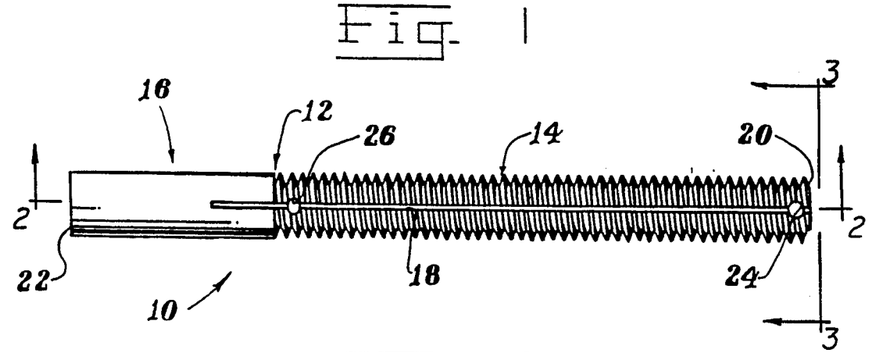
FIG. 1 is a top view of an apparatus of the present invention in one embodiment, absent a corresponding conduit.
Figure 2:
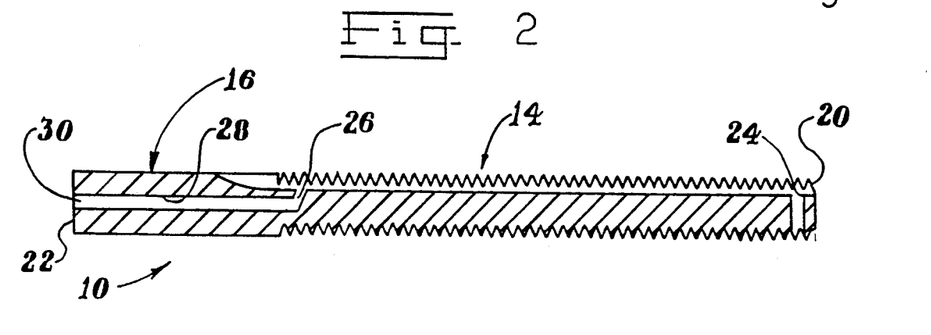
FIG. 2 is a cross-sectional view of the apparatus of FIG. 1, taken along line 2—2.

Turning now to FIG. 1, the first embodiment 10 includes a support member 12 which is comprised of a first, single-flight threaded portion 14 and a second, unthreaded portion 16. A groove 18 is defined in the member 12 which cuts through the threads of threaded portion 14 from a first end 20 of the member 12 toward a second end 22 of the member 12 (see FIGS. 2 and 3).

A first hole 24 is defined through the member 12 adjacent the first end 20 and in communication with the groove 18, while a second hole 26 is defined in the threaded portion 14 near its boundary with the unthreaded portion 16 of member 12.

This second hole 26 preferably extends into the support member 12 at an angle, and terminates in a central channel 28. Channel 28 defines an opening 30 into the core of member 12 at the second end 22 of member 12, and extends generally along the longitudinal axis of member 12, terminating at some point short of intersecting with the first hole 24 but at least being in communication with the second hole 26.

Figure 4:
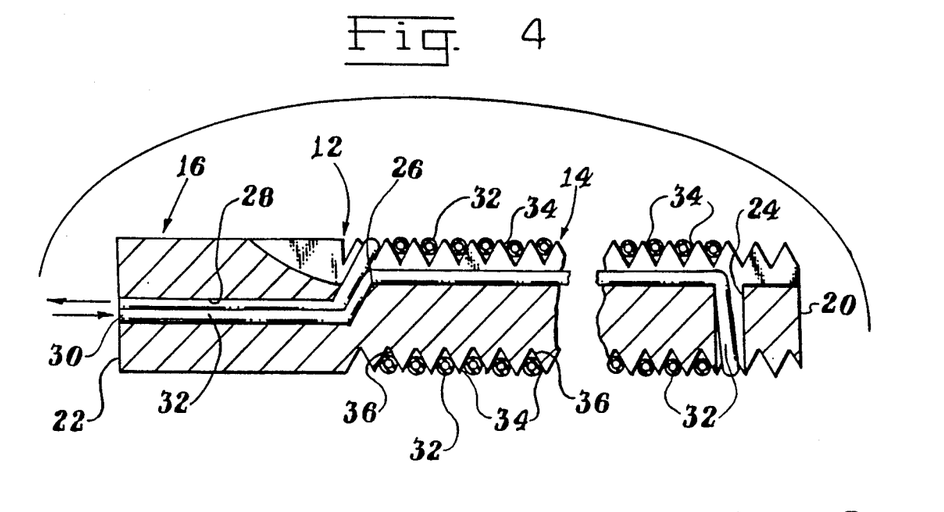
FIG. 4 is an enlarged cross-sectional view of the apparatus as depicted in FIG. 2 with a capillary membrane added.

The manner in which a capillary membrane or other conduit is supported by the support member 12 is shown in FIG. 4. In FIG. 4, a capillary membrane 32 feeds from a source of a receiving fluid (not shown) through opening 30 at the second end 22 of member 12, and extends through central channel 28 and the second hole 26.

On exiting channel 28 through the second hole 26, the membrane 32 traverses the threaded portion 14 of member 12 via the groove 18 until the first hole 24 is reached. The membrane 32 then feeds through the hole 24 and begins winding its way back along the length of the member 12 through successive flights in the threaded portion 14, while being positioned and supported wholly within such flights in the sense that no portion of the membrane 32 in a flight extends above the thread crests 34 defining the flight on either side.

In this way potentially damaging particulates or debris in a matrix stream in which the supported membrane 32 is immersed come into contact with the crests 34 rather than the membrane 32. In a similar fashion, the membrane 34 is protected from the elongating or distorting influence of the surrounding matrix stream due to the support provided by the flanks 36 of adjacent threads. Where the matrix stream to be monitored has a relatively high flow rate and is likely to exert a good deal of force on an unsupported membrane, as will be the case in many process streams of interest for monitoring and control, this feature is likely to be of significant value.

As the membrane 32 reaches the second hole 26 from which it (i.e., the membrane 32) originally emerged, the membrane 32 is fed back through the hole 26 and channel 28 and emerges from the opening 30.

The membrane tubing 32 is then placed in fluid communication with means for analyzing a stream of receiving fluid circulated through the membrane 32 in use of the apparatus, preferably by tubing or some other means which is inert to, and which does not interfere with, transmission of the selected materials received from a matrix stream in which the supported membrane 32 (or other conduit) has been placed. Depending on the nature of the materials to be collected from the matrix stream and of the receiving fluid, the analytical means employed can include, for example, a gas chromatograph with mass spectrometer or a liquid chromatograph.

In another, more preferred embodiment 38 of the apparatus which is shown in FIGS. 5–7 and 10, a support member 40 has a double-lead flight threaded portion 42 and an unthreaded portion 44. Two channels 46 and 48 are defined longitudinally through the unthreaded portion 44, and emerge at a shoulder 50 of the unthreaded portion 44 in position to receive from or transmit to a helical flight of the adjacent threaded portion 42 a membrane 52 supported therein. Short, curving transition channels (not shown) may preferably be provided in the surface of the unthreaded portion 44 adjacent the shoulder 50 for easing the transition of the membrane 52 between the channels 46 and 48 and the flights of the threaded portion 42. Preferably capillary membrane ends placed in these channels 46 and 48 are adapted to be joined in secure fluid communication with a source (not shown) of a receiving fluid and with a gas or liquid chromatograph (also not shown) or the like, respectively.

Figure 10:
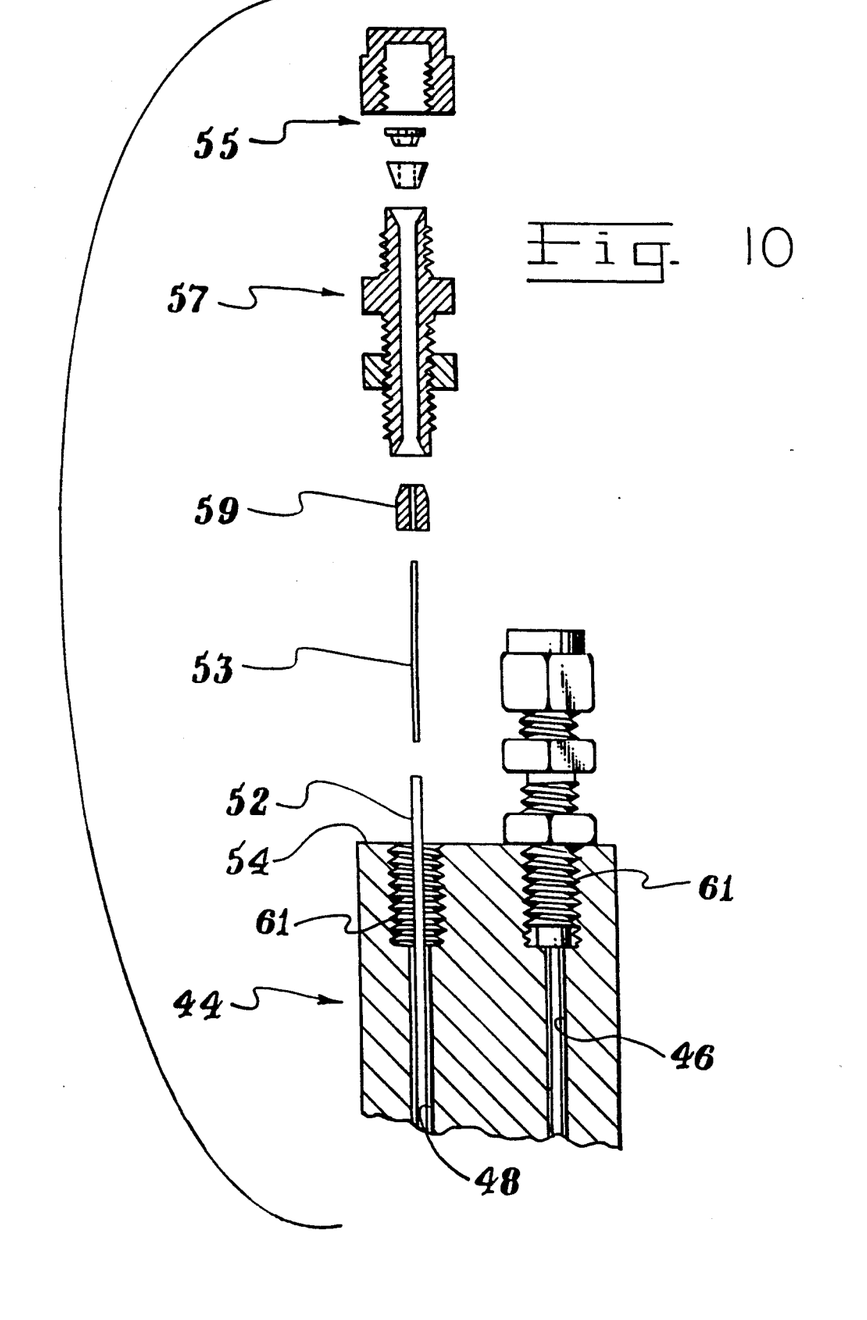
FIG. 10 shows a preferred manner of joining an apparatus of the type shown in FIGS. 5-7, a source of a receiving fluid and an analytical apparatus in fluid communication.

The presently preferred construction for joining the membrane 52 in communication with a source of a receiving fluid, and in turn with a gas or liquid chromatograph or the like, is shown in FIG. 10, wherein one end of a length of membrane support tubing 53 is inserted into and holds open the central lumens of the membrane tubing 52. This membrane support tubing 53 can be made of, for example, stainless steel or a fused silica glass.

Membrane support tubing 53 is in turn securely joined via a two ferrule compression-type fitting 55 to a conventional tubing lead (not shown, and comprised, e.g., of stainless steel or nickel) to the gas or liquid chromatograph. A compression-type tube-to-tube bulkhead fitting 57 ties the assembly 55 and a membrane sealing ferrule 59 into an integrated whole, with the fitting 57 being joined to the support member 40 by the threaded engagement of fitting 57 with a threaded portion 61 of a channel 46 or 48 in the unthreaded portion 44 of support member 40.

The membrane tubing 52 associated in use with the support member 40 thus enters the unthreaded portion 44 through channel 46 from a second end 54 of the member 40 and from a source of the receiving fluid to be employed in membrane 52.

Returning now to FIGS. 5–7, the membrane 52 is then wrapped around the support member 40 through alternating flights 56 (FIG. 5) toward a first end 58 of member 40, with the membrane 52 being positioned and supported wholly within the flights 56 as in the embodiment of FIGS. 1–4.

Figures 3, 6, 7:
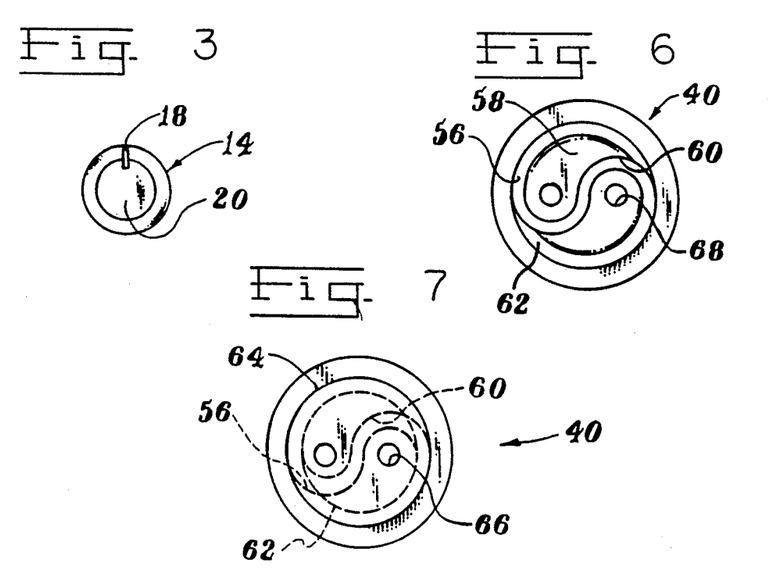
FIG. 3 is an end view of the apparatus of FIG. 1, taken from the perspective of line 3—3.
FIG. 6 is a sectional view of the embodiment of FIG. 5, taken along line 6—6.
FIG. 7 is an end view of the embodiment of FIG. 5, as taken from the perspective of line 7—7.

At the first end 58 of the support member 40, and as best shown in FIG. 6, the membrane 52 then travels through an S-shaped channel 60 in the first end 58 of the support member 40 which joins the alternating helical return flights 62 in communication with the flights 56. The membrane 52 in traversing flights 62 thus is wrapped around member 40 through those alternating flights which had been "skipped" in going from the second end 54 of the member 40 to the first end 58 of member 40.

The membrane 52 returns to and is received by the channel 48 in the unthreaded portion 44 of the support member 40. The receiving fluid and any selected materials collected by the membrane 52 and carried by the receiving fluid are communicated through channel 48 to a gas or liquid chromatograph, preferably by the arrangement depicted in FIG. 10 and described above.

Figure 5:
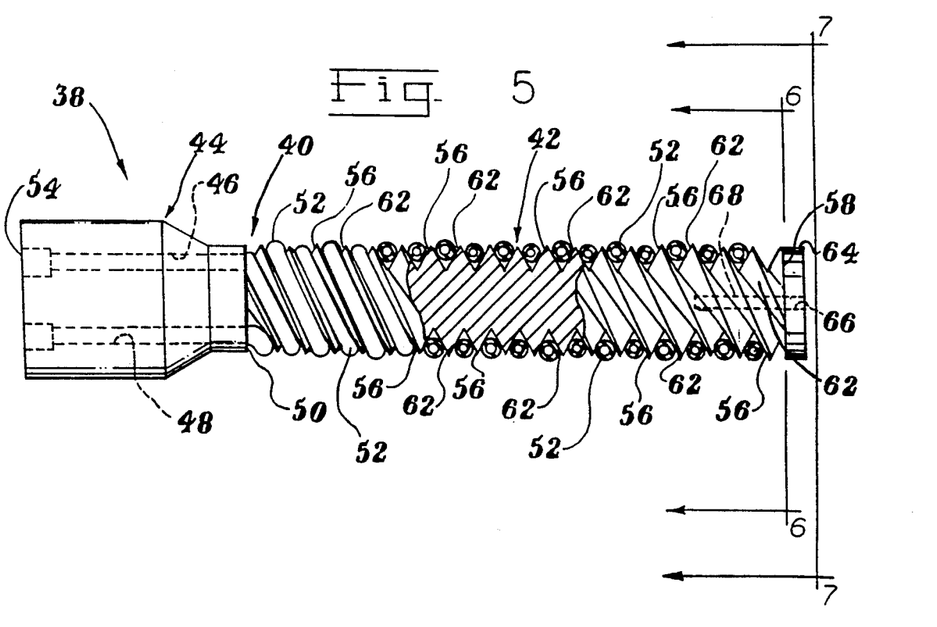
FIG. 5 is a side view in partial cross-section of an alternative, preferred embodiment of the apparatus of the present invention.

A protective cap 64 is placed over the S-shaped channel 60 in the first end 58 of the support member 40, and is conventionally joined to the support member 40 as through bolts or screws placed through holes 66 in the cap 64 and corresponding holes 68 in the first end 58 of support member 40. The function of protective cap 64 is to help contain the membrane 52 in the S-shaped channel 60, and further to protect the membrane 52 in the S-shaped channel 60 from damage should the apparatus be inserted too far into a process pipe, for example, and encounter the opposite wall of the pipe (assuming a preferred, generally transverse presentation or insertion with respect to the matrix stream, as opposed to an axial insertion) or should the apparatus' first end 58 encounter some other obstacle on insertion.

It may also be desirable to employ the cap 64 as a spacer of sorts, wherein the cap 64 would be sized so that when the first end 58 is placed against a pipe wall or the like, the membrane 52 in the threaded portion 42 of the member 40 would be precisely and controllably positioned in the matrix stream, as for example to avoid encountering fouling on the inside walls of the pipe. It should be observed that while the protective cap 64 is illustrated only with respect to the embodiment of FIGS. 5–7, a similar protective cap or spacer could be readily employed in the embodiment of FIGS. 1–4.

In use of either of the two embodiments depicted in FIGS. 1–7, a portion of the capillary membrane or other conduit associated with a device is exposed to a complex process stream or aggregation of flowable materials in a pipe, reactor or other process vessel (the stream or aggregation containing or carrying one or more selected materials therein of interest) by inserting the first end of the device into the stream or aggregation. Where the process stream is of a character and/or flow rate which is likely to damage a bare, unsupported membrane, then at least that portion of the membrane exposed to the process stream is positioned and supported substantially wholly (and preferably wholly) within a groove defined in the device and extending from the first end of the device toward the second, external end of the device.

"Groove" in this sense and as used elsewhere herein embraces the threaded flights of either of the embodiments shown in FIGS. 1–7, but is not limited thereto. What is intended for purposes of the present invention and disclosure is that those portions of a capillary membrane (or other conduit) which are immersed in and exposed to potentially damaging or distorting environments should be protected from these environments, by being supported and positioned within a recessed portion of the body of a support member.

It is advantageous, however, for improving the overall sensitivity of the devices shown in FIGS. 1–4 and 5–7 that the portion of membrane available for insertion into a process stream or aggregation be longer, rather than shorter, for a given membrane so that the contact area between the membrane and stream or aggregation is increased. A greater contact area permits the recovery of a greater amount of a given low-level material in a stream over a given length of time, and consequently enables the more timely and effective monitoring of such a material. A continuous groove in the form of threads on a support member is for this reason to be preferred over a groove proceeding more directly from the first end toward the second, external end of the device. For this reason as well, it is considered that the double-lead flight threaded embodiment of FIGS. 5-7 (in which the threaded flights going from the second end to the first end, and from the first end back toward the second end may be thought of as two connected grooves) will normally be preferred over the single flight threaded construction of FIGS. 1-4.

By similar reasoning, normally it will be desirable: (a) for the groove carrying the membrane in a given apparatus to extend from the first, internal end of the support member to an interior wall of the process pipe, reactor or other vessel in which the apparatus is used, or where the stream in question does not substantially fill a pipe or vessel to such interior wall, at least to span as much of the matrix stream as possible and as consistent with the effective use of the device (see in this regard the earlier discussion of the protective cap as a spacer); and (b) for the membrane carried within such groove to be essentially coextensive with the groove.

Thus, in the embodiment of FIGS. 1-4 the threaded portion 14 of member 12 is preferably designed to extend from its first end 20 to an interior wall of a pipe, reactor or other vessel into which the apparatus is inserted, and the second hole 26 into which the membrane 32 returns is preferably near the interface of the unthreaded and threaded portions 16 and 14, respectively, of the member 12. Similarly, the interface between the threaded and unthreaded portions 42 and 44 of the more preferred embodiment is preferably designed to correspond to an interior wall of a vessel or pipe in which the apparatus is employed.

As perhaps best illustrated in schematic fashion with respect to the on-line calibration apparatus shown in FIG. 8 and described more particularly below, as the membrane of an apparatus 10 or 38 is exposed to the matrix stream within a process pipe 74 and to the one or more selected materials of interest therein, an appropriate receiving fluid (which may be either a gas or liquid) is circulated through the central lumens of the membrane. The materials to be collected by the membrane from the matrix stream permeate or diffuse through the walls of the membrane and into a receiving fluid, and the receiving fluid carries the collected materials to some analytical means 71, such as a gas chromatograph/mass spectrometer combination or a liquid chromatograph.

The circulation of the receiving fluid and/or the analysis of the receiving fluid from the membrane of a device may be manually initiated, or one or both may preferably be initiated by some conventionally-known remote automated means 73 for accomplishing this function so that sampling and analysis of the process stream may be more conveniently done. Suitable apparatus are described, for example, in *Automated Stream Analysis For Process Control*, Vol. 1 (Academic Press, Manka ed., 1982) and Nichols, *On-Line Process Analyzers* (John Wiley and Sons, 1988), with such publications being incorporated herein by reference in pertinent part.

It will be preferred in many applications, also, that the means 71 for analyzing the receiving fluid from the membrane be coupled to some sort of process control, for example, to any conventionally-known means 75 for altering the course and/or composition of the stream being monitored responsive, for example, to the presence in the stream of a given concentration of one or more selected materials.

In terms of characterizing the capillary membranes (or other conduits generally), support members, receiving fluids and analytical devices useful in the present invention, all of these elements are application-dependent and it is considered that those skilled in the art will be well able to select an appropriate combination of these elements for a given application without undue experimentation.

With respect to the tubular membranes useful in the present invention, it is believed that permeation membrane or diffusion membrane tubing may variously be used and selected depending on the intended application of the apparatus.

It will generally be preferred for a given membrane that the wall thickness of the membrane be selected to be as thin as possible to keep the membrane intact and the central lumens of the membrane fully open throughout the membrane's length.

The support member can be made of any number of materials, but preferably will be inert to its environment and will have a degree of chemical resistance and resistance to wear by flowing particulates or debris appropriate to the stream in which the support member is to be immersed. At the same time, the material for the support member should ideally be relatively inexpensive and should machine well so that the threads, channels, grooves and the like of the support member may be incorporated therein without undue expense or difficulty.

For devices employing a tubular membrane as the conduit, the receiving fluid can be either a gas or a liquid. The particular gas or liquid is not critical to the invention as long as the material received through the membrane is either volatile in the gas or soluble in the liquid receiving fluid used, and as long as the receiving fluid itself does not appreciably permeate or diffuse out through the membrane. When the receiving fluid is a liquid, then the analytical means employed for the receiving fluid can comprise a liquid chromatograph. When the receiving fluid is a gas, then the analytical means preferably comprises, for example, a gas chromatograph and mass spectrometer.

Standardization of the apparatus in an on-line, process control context can be done in a couple of ways, depending on whether one may safely and practicably open a process pipe or vessel and insert the apparatus, or whether external standardization of the device is feasible.

Where external standardization of the device is feasible and can be safely done, the device may conveniently be designed and sized to be insertable through a gate valve or the like into a process pipe or vessel. Standardization of this embodiment may simply involve immersing and stirring the device in a bucket of water or other matrix containing a known concentration of a material of interest.

It will generally be preferable for the support member of this valve-insertable device to be coupled, or to be at least capable of being coupled, to a stinger which is also insertable through a standard gate valve to a process conduit or vessel. In practical terms, this will involve sizing the unthreaded portions of the probe embodiments of FIGS. 1-4 and 5-7 to be joinable to a length of conventional piping by a piping union, with a ferrule having been placed around the unthreaded portion of the probe. The leads to and from a source of a receiving fluid and the particular analytical means employed in an apparatus can then preferably be protected by running these leads through the length of piping.

Where the process pipe, reactor or vessel is pressurized or under a vacuum, for example, or where there is a need to limit the exposure or risk of exposure of a person taking the measurement of the stream or aggregation in question to such stream or aggregation, then an on-line standardization of the device is appropriate.

Figure 8:
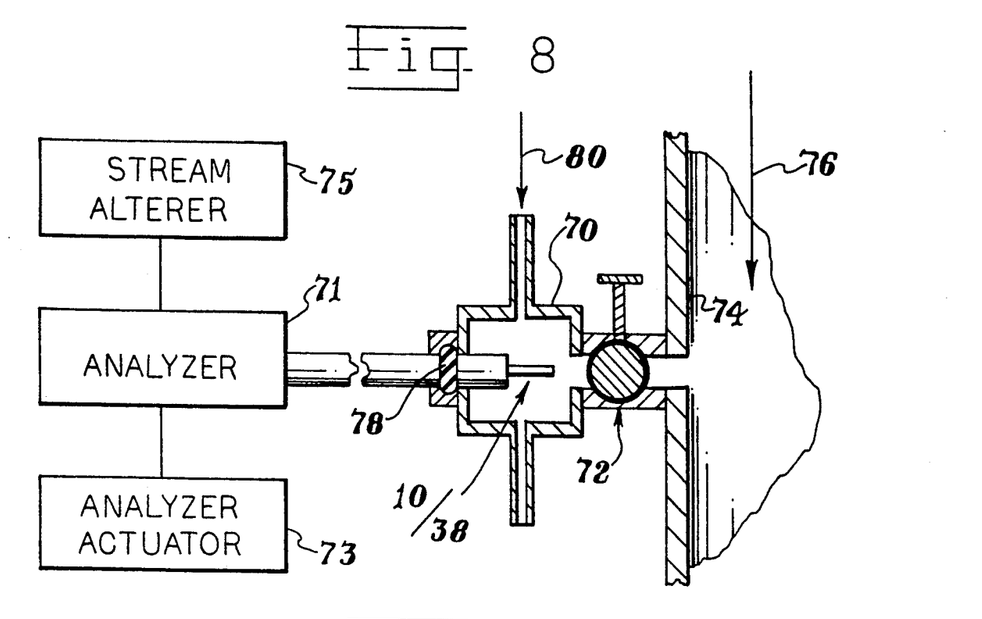
FIG. 8 is a cross-sectional view of an apparatus for on-line calibration in a process control context of a device of the types shown in FIGS. 1-4 and 5-7.

This on-line standardization can be accomplished with the same value-insertable embodiment of the apparatus by constructing, as shown in FIG. 8, an external calibration or standardization chamber 70 in communication with a valve 72 and positioned opposite the process pipe or vessel 74 containing the stream 76 to be monitored. The valve-insertable device 10 or 38 of the present invention is passed into the calibration chamber 70 through a sliding seal 78; when the valve 72 is closed, the device 10 or 38 is isolated from the process pipe or vessel 74 so that a standard flow 80 may be passed through the chamber 70. The device (10 or 38) may then be moved directly into the process pipe or vessel 74 by opening the valve 72 and inserting the device through the open valve 72. The sliding seal 78 by which the device is entered into the calibration chamber 70 prevents the contents of the pipe, reactor or vessel 74 from coming into contact with a person employing the device.

Figure 9:
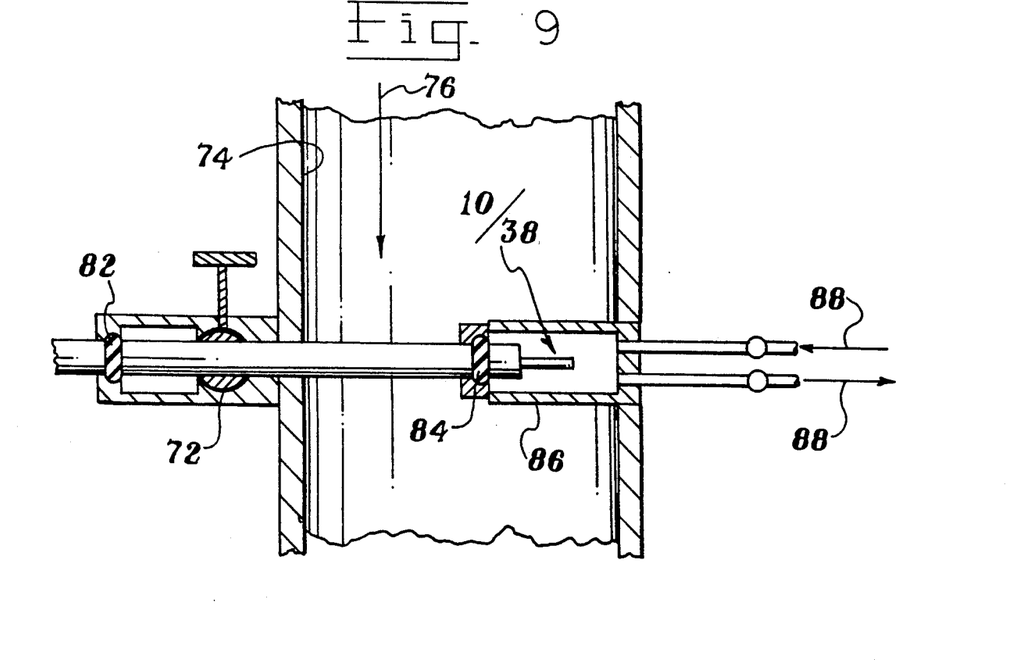
FIG. 9 is a cross-sectional view of an alternate apparatus for the on-line calibration of a device of the types shown in FIGS. 1-4 and 5-7.

Alternately, and as shown in FIG. 9, a first sliding seal 82 may be provided adjacent the valve 72 to permit the valve 72 to be safely opened and the device 10 or 38 inserted therethrough. For calibrating the device 10 or 38, the device is passed through a second sliding seal 84 into an internal standardization chamber 86 defined in the pipe 74, which chamber 86 receives a standard flow 88 therethrough. In still another method, a standard (such as an inert gas or an isotopically-labeled analog of a compound in the process stream) is merely injected into the process pipe 74 upstream of the device 10 or 38. Another method might involve intermittently analyzing a standard in a standardization chamber 70 or 86 while continuously introducing an internal standard upstream of the device 10 or 38.

The apparatus of FIGS. 1-7 and 10 are adaptable to a wide variety of applications. For example, the support member in either embodiment 10 or 38 could conceivably be adapted and sized on the level of a hypodermic needle for in vivo use in such hostile environments as the gastrointestinal tract. And, as has already been suggested above, by using an optical fiber as the conduit around a support member, the apparatus of the present invention could be used in the determination of species by attenuated total reflectance techniques.

Discussion thus far has focused on use of the apparatus of the present invention in the body of a matrix stream or aggregation of flowable materials. In certain instances it may be necessary or desirable to insert the apparatus into a slipstream taken from the matrix stream, however, and for purposes of the defining claims below a slipstream of the matrix stream should be considered as embraced within the confines of "a matrix stream or aggregation of flowable materials". A suitable flow cell apparatus 90 (a type of "process pipe, . . . or other process vessel" as recited in the claims below) for utilizing an apparatus of the present invention in this fashion is shown in FIG. 11.

Figure 11:
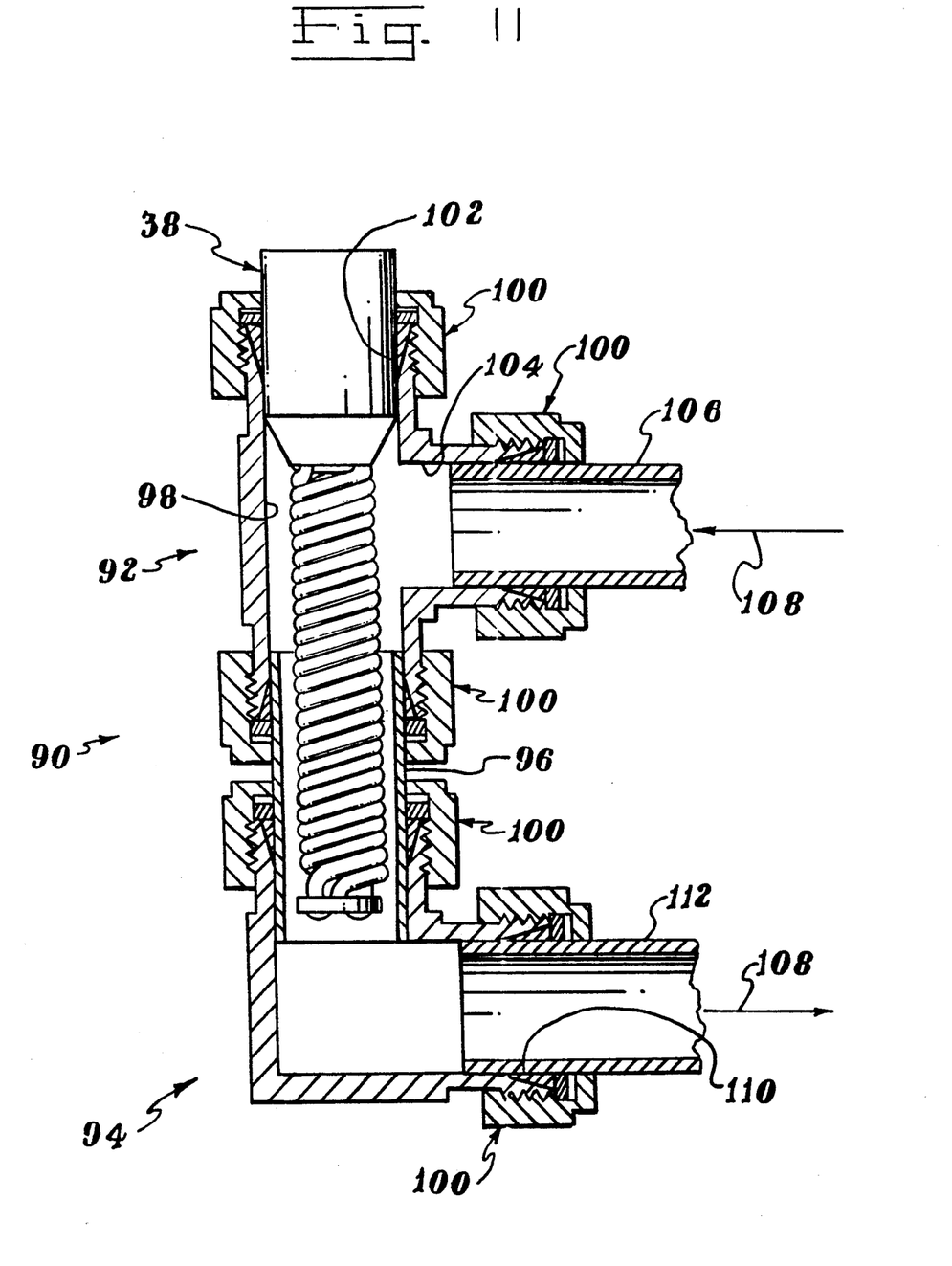
FIG. 11 is a partially cross-sectional view of a flow cell apparatus which employs an apparatus as shown in FIGS. 5-7 for analyzing a slipstream off a larger process stream.

Referring now to FIG. 11, the flow cell apparatus 90 broadly comprises a standard piping tee portion 92, an elbow portion 94 and a length 96 of piping joining the tee and elbow portions 92 and 94. A device 10 or 38 of the present invention (a probe device 38 being shown) extends coaxially through a cylindrical bore portion 98 of the tee portion 92, and with a ferrule and threaded nut assembly 100 caps off one opening 102 of the tee portion 92. Side arm 104 of tee portion 92 is coupled via a second ferrule and threaded nut assembly 100 to a pipe 106 from a matrix/process stream, so that a slipstream 108 may be taken from the matrix stream through pipe 106 and along the device 38 in tee portion 92.

This slipstream 108 continues along the device 38 and through the length 96 of piping joining the tee and elbow portions 92 and 94, respectively, and exits through a downstream end 110 of the elbow portion 94. The length 96 of piping is joined through ferrule and threaded nut assemblies 100 at either of its ends to the respective tee and elbow portions 92 and 94, while a return pipe 112 (for returning the slipstream 108 to the matrix stream) is joined to the downstream end 110 of elbow portion 94 via a final ferrule and nut assembly 100.

A more complete understanding of the present invention can be gained from the illustrative examples offered below:

EXAMPLE 1

Trace levels of chloroform (about 0.1 to about 1.0 parts per million by weight) were found to be present in a hot (50 to 60 degrees Celsius) aqueous plant stream containing from 2 to 3 weight percent of hydrochloric acid and suspended particulate matter.

For this example, a comparison was made between a stream analysis as performed by a laboratory purge and trap instrument set up in accordance to EPA Method 601/602, "Analysis of Volatile Organics in Water", and an analysis as performed by a preferred, valve-insertable apparatus of the present invention (corresponding to FIGS. 5-7 and 10) in combination with a conventional laboratory gas chromatograph.

The valve-insertable apparatus for this example employed a silicone rubber capillary membrane. The membrane length was six (6) feet and the membrane had an outside diameter of 0.025" and an inside diameter of 0.012", for an effective internal volume of about 0.1 ml. The membrane was coupled to a conventional laboratory gas chromatograph via $\frac{1}{8}$" stainless steel tubing, and the apparatus or probe was fully immersed in the process stream through an open trough, using a six (6) foot-long piece of 1" piping coupled by a piping union to the probe.

Nitrogen was circulated through the central lumens of the membrane at 6 cubic centimeters per minute, and carried to an automated sample valve. The sample loop was injected onto the chromatographic column, and stream components were separated and quantitated on a flame ionization detector.

Samples for the purge and trap analysis were captured in liquid-full, virgin glass bottles with polymeric seal tops. The fresh samples were plunged into an ice bath and transported immediately to the site of the purge and trap apparatus, whereupon the samples were loaded directly into the purge and trap auto-sampler and analyzed.

Figure 12:
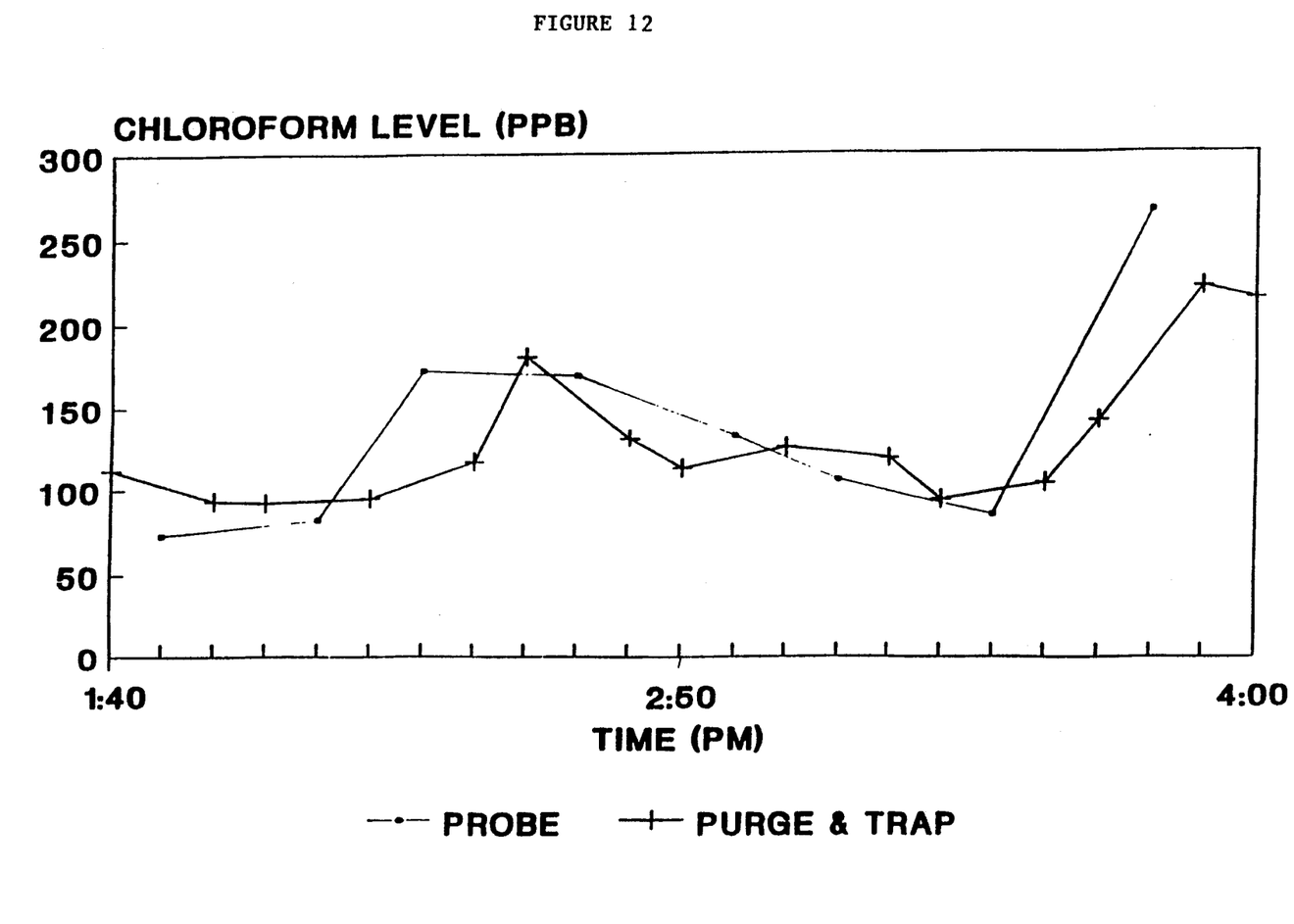
FIG. 12 is a graphic representation of the results of Example 1 below.

FIG. 12 shows the quantitated levels of chloroform obtained by purge and trap analysis and by an apparatus of the present invention, and suggests that on-line analysis using the apparatus of the present invention should be an acceptable alternative to the off-line and significantly more inconvenient purge and trap analysis suggested by the Environmental Protection Agency (EPA).

EXAMPLE 2

An azeotrope was formed in a process stream between 1,3 butadiene and trace levels of acetaldehyde and acetone. To remove these trace level impurities and permit recovery of the 1,3 butadiene, it was proposed to contact the crude 1,3 butadiene process stream with water, whereby the carbonyl-containing impurities could be extracted into the aqueous phase. Conventional direct analysis was attempted (at 70 lbs. of pressure and 60 degrees C.) in a conventional on-line gas chromatograph of the crude and purified 1,3 butadiene process streams to monitor and control the extraction/separation, but was plagued with plugging and fouling problems due to polymerization of the 1,3 butadiene and the presence of coke-like particles.

Figure 13:
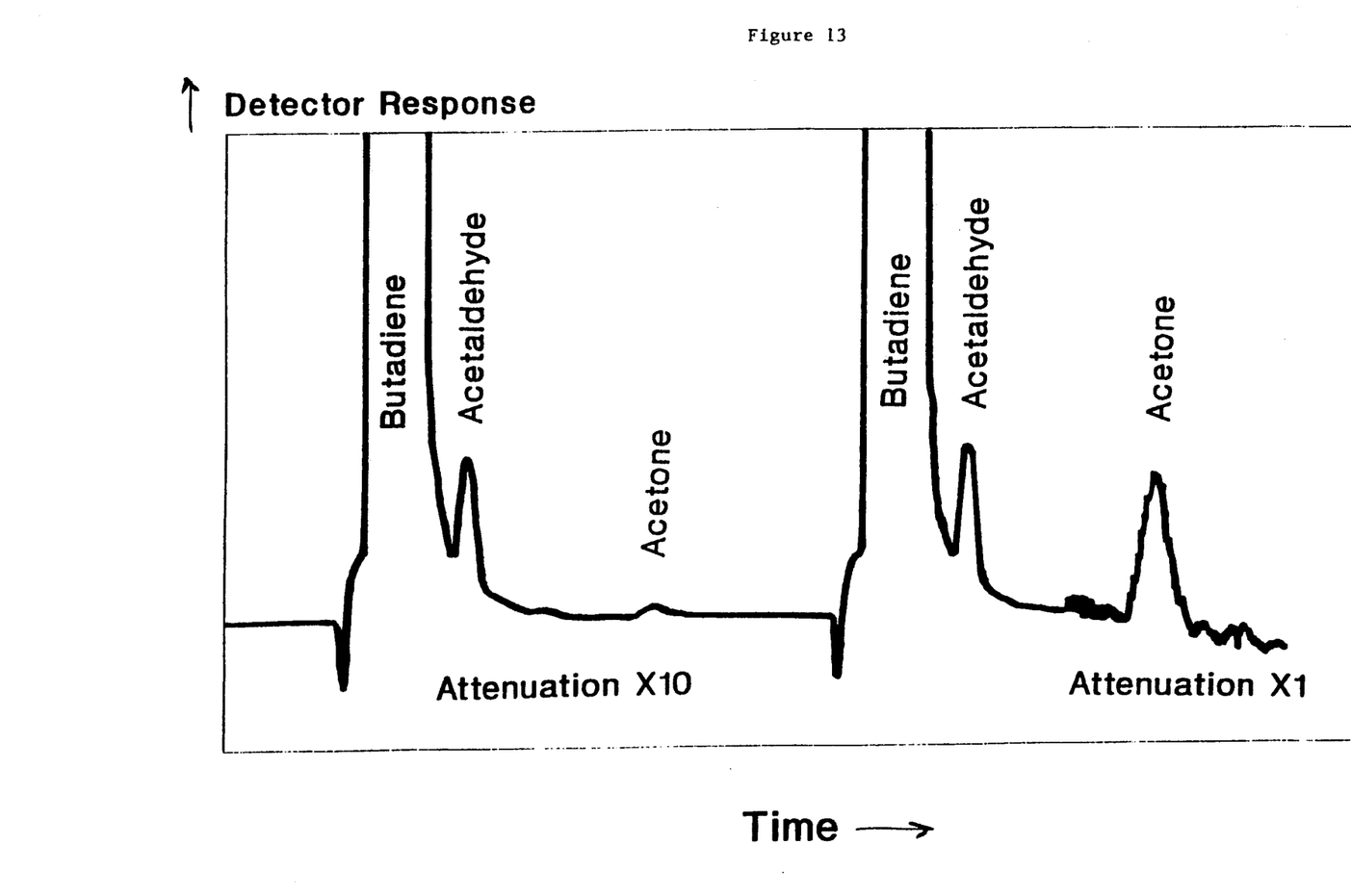
FIG. 13 shows the results obtained in Example 2 below.

A capillary membrane sample probe of the present invention was constructed as shown in FIGS. 1-4 and as described herein, but rather than the silicone rubber membrane of Example 1 employed a Teflon* FEP copolymer membrane tubing (six (6) feet long, 0.025" o.d., 0.012" i.d., 0.1 ml internal volume). The probe was employed in a flow cell apparatus of the type shown in FIG. 11, and an emulsified slipstream of water and 1,3 butadiene (essentially water-saturated 1,3 butadiene) was passed through the flow cell. Nitrogen gas, flow controlled at 6 cc/min., was continuously circulated through the probe and delivered to a sampling valve in a gas chromatograph as in Example 1. The sample loop on the sampling valve was injected onto the column of the GC, and separated and enabled the quantification of the 1,3 butadiene, acetaldehyde and acetone in the crude and purified process streams as shown in FIG. 13.

EXAMPLE 3

An incoming waste stream to a biological wastewater treatment facility was a potential source of benzene, a tightly permitted, essentially non-biodegradable pollutant. With the dilution from other incoming wastewater streams, it was determined that the concentration of benzene in the particular waste stream should not exceed 2 parts per million by weight.

Figure 14:
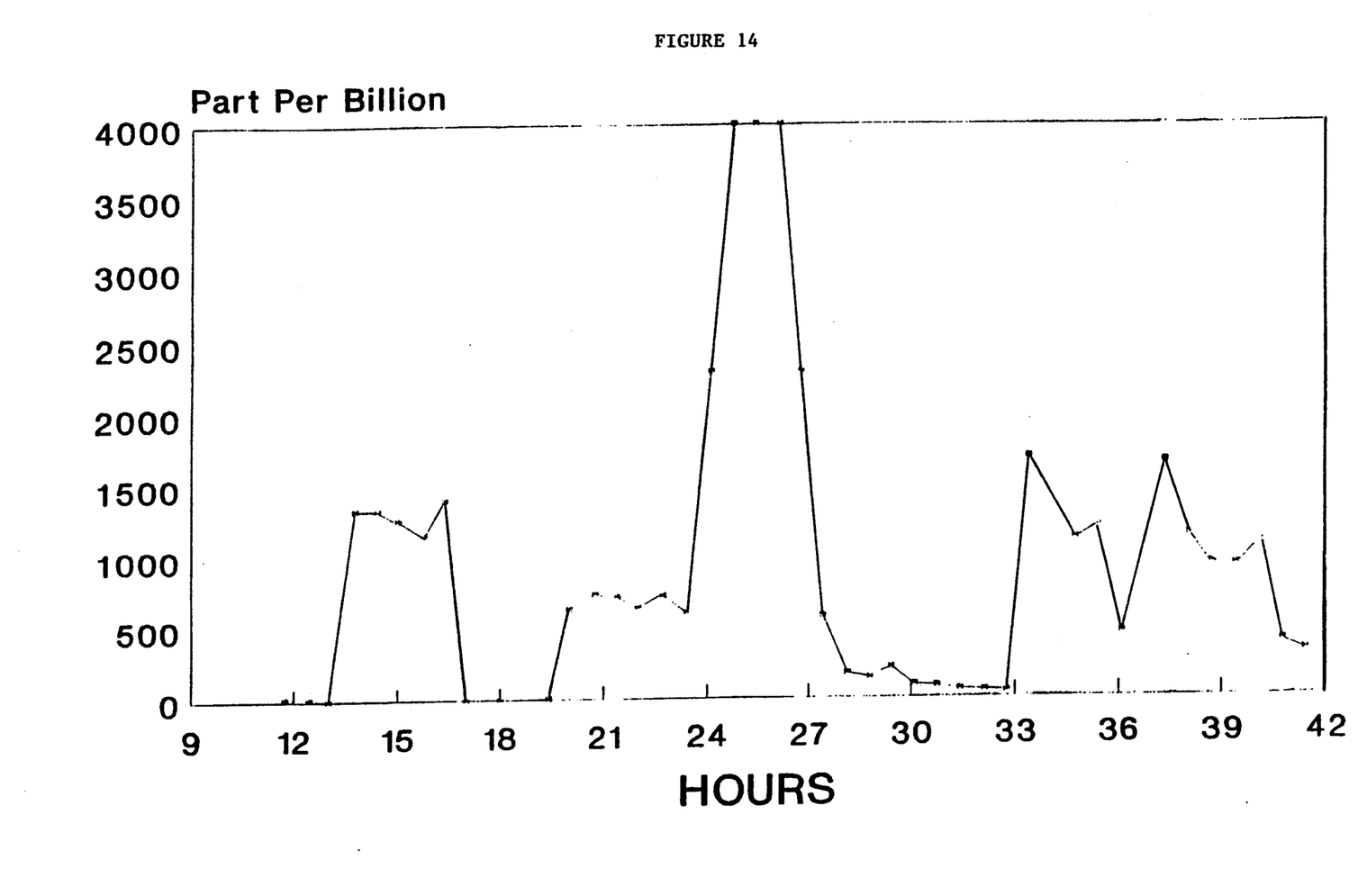
FIG. 14 graphically summarizes the results of Example 3.

A capillary membrane sample probe was constructed for this example as in FIGS. 1-4 and as in Example 2 above. This sample probe was inserted through a six (6) inch gate valve directly into the waste stream for monitoring (with a conventional gas chromatograph) the levels of benzene therein. FIG. 14 shows the concentrations of benzene in the waste stream over a two day period of such monitoring.

An excursion in the benzene level of the stream was observed at between 21 and 26 hours, with the probe and associated GC tracking the rise in benzene concentration. The plant producing the waste stream was notified, and at 27 hours the source plant removed all possible benzene sources to the stream. The benzene concentration thereafter was observed to fall to near zero. At 31 hours, the source plant informed wastewater treatment plant personnel that the upset had been diagnosed and corrected, and the various flows into the waste stream were resumed. The membrane sampling probe and associated GC subsequently confirmed the levels of benzene as returning to appropriate levels, indicating that the problem had indeed been remedied at the source plant.

While preferred embodiments have been specifically illustrated, described and/or exemplified herein, those skilled in the art will recognize that numerous changes and modifications may be made to these embodiments which are nevertheless within the scope and spirit of the present invention, and which are accordingly intended to be embraced by the claims following hereafter.

What is claimed is:

1. An apparatus for use in determining the presence and/or concentration of one or more selected materials in a matrix stream or aggregation of flowable materials within a process pipe, reactor or other process vessel, comprising:

a support member having a first, internal end for inserting into the matrix stream or aggregation of flowable materials when the apparatus is placed in service and a second end positioned externally of the pipe, reactor or other process vessel in use, and wherein the support member underlies and defines a groove in and along an external surface thereof of which at least a portion extends into the matrix stream in use; and a conduit which is adapted to be placed in communication with an analytical device external of the process pipe, reactor or other process vessel and which is positioned and supported substantially wholly within at least that portion of the groove in the support member extending into the matrix stream or aggregation in use, whereby the conduit may be placed in contact with the matrix stream or aggregation of flowable materials while being protected by and supported within such groove portion.

2. An apparatus as defined in claim 1, wherein the conduit is positioned and supported wholly within the groove.

3. An apparatus as defined in claim 1, wherein the groove extends continuously from an interior wall of the pipe, reactor or other process vessel to the first, internal end of the support member, and from the first end to the interior wall.

4. An apparatus as defined in claim 3, wherein the conduit is positioned and supported wholly within the groove.

5. An apparatus as defined in claim 4, wherein the conduit is generally coextensive with its supporting groove.

6. An apparatus as defined in claim 1, wherein the groove extends continuously from an interior wall of the pipe, reactor or other process vessel to the first internal end of the support member, and wherein the support member defines a second groove therein in communication with the first groove which extends continuously from the first internal end of the support member to the interior wall.

7. An apparatus as defined in claim 6, wherein the conduit is positioned and supported wholly within the first and second grooves of claim 4.

8. An apparatus as defined in claim 7, wherein the conduit is generally coextensive with its supporting first and second grooves.

9. An apparatus as defined in claim 8, wherein the first and second grooves of the support member consist of alternating helical flights of a double lead threaded support member, and wherein the conduit is positioned generally in the troughs of such flights and is flanked by the walls defining the flights of the support member, the crests of the walls on either side of the conduit in a respective flight extending above the trough and laterally from the support member to a greater extent than the conduit.

10. An apparatus as defined in claim 9, wherein the apparatus is adapted and sized to be insertable through a standard-size valve into the pipe or vessel.

11. An apparatus as defined in claim 9, wherein the conduit is a tubular membrane, and the apparatus further comprises means for communicating the one or more materials collected from the matrix stream or aggregation of flowable materials by the tubular membrane to an analytical device.

12. An apparatus as defined in claim 9, further comprising a protective spacer attached to the support member at the first, internal end of the support member.

13. An apparatus as defined in claim 9, wherein the support member is joinable to a length of standard piping via a piping union.

14. An apparatus as defined in claim 6, wherein the apparatus is adapted and sized to be insertable through a standard-size valve into the pipe or vessel.

15. An apparatus as defined in claim 6, wherein the conduit is a tubular membrane, and the apparatus further comprises means for communicating the one or more materials collected from the matrix stream or aggregation of flowable materials by the tubular membrane to an analytical device.

16. An apparatus as defined in claim 6, further comprising a protective spacer attached to the support member at the first, internal end of the support member.

17. An apparatus as defined in claim 6, wherein the support member is joinable to a length of standard piping via a piping union.

18. An apparatus as defined in claim 1, wherein the apparatus is adapted and sized to be insertable through a standard-size valve into the pipe or vessel.

19. An apparatus as defined in claim 1, wherein the conduit is a tubular membrane, and the apparatus further comprises means for communicating the one or more materials collected from the matrix stream or aggregation of flowable materials by the tubular membrane to an analytical device.

20. An apparatus as defined in claim 1, further comprising a protective spacer attached to the support member at the first, internal end of the support member.

21. An apparatus as defined in claim 1, wherein the support member is joinable to a length of standard piping via a piping union.

22. An apparatus for use in determining the presence and/or concentration of one or more selected materials in a matrix stream or aggregation of flowable materials within a process pipe, reactor or other process vessel, comprising:

a support member having a first, internal end for inserting into the matrix stream or aggregation of flowable materials when the apparatus is placed in service and a second end positioned externally of the pipe, reactor or other process vessel in use, and wherein the support member underlies and defines a groove in and along an external surface thereof of which at least a portion extends into the matrix stream in use;

a conduit positioned and supported substantially wholly within at least that portion of the groove in the support member which extends into the matrix stream or aggregation in use, whereby the conduit may be placed in contact with the matrix stream or aggregation of flowable materials while being protected by and supported within such groove portion; and analytical means, associated and in communication with the conduit in use, for determining the presence and/or concentration of the one or more selected materials.

23. An apparatus as defined in claim 22, further comprising means for remotely actuating the analyzing means.

24. An apparatus as defined in claim 23, further comprising means for altering the course and/or composition of the matrix stream or aggregation of materials responsive to the presence of a given concentration of the one or more selected materials in said matrix stream or aggregation.

25. An apparatus as defined in claim 22, further comprising means for altering the course and/or composition of the matrix stream or aggregation of materials responsive to the presence of a given concentration of the one or more selected materials in said matrix stream or aggregation.

* * * * *